United States Patent
Baumoeller et al.

[11] Patent Number: 5,888,487
[45] Date of Patent: Mar. 30, 1999

[54] LOW-VISCOSITY OPACIFIER CONCENTRATES

[75] Inventors: Guido Baumoeller, Duesseldorf; Armin Wadle, Hilden; Achim Ansmann, Erkrath; Holger Tesmann, Juechen; Thomas Foerster, Erkrath, all of Germany

[73] Assignee: Henkel Kommanditgesellschaft auf Aktien, Duesseldorf, Germany

[21] Appl. No.: 930,570

[22] PCT Filed: Mar. 20, 1996

[86] PCT No.: PCT/EP96/01197
   § 371 Date: Oct. 31, 1997
   § 102(e) Date: Oct. 31, 1997

[87] PCT Pub. No.: WO96/30476
   PCT Pub. Date: Oct. 3, 1996

[30] Foreign Application Priority Data

Mar. 29, 1995 [DE] Germany ............... 195 11 572.4

[51] Int. Cl.⁶ .................. A61K 9/14; A61K 9/50
[52] U.S. Cl. .......... 424/70.1; 424/499; 424/501; 424/502; 424/489
[58] Field of Search ................. 424/489, 490, 424/493, 497, 498, 499, 501, 502, 70.1

[56] References Cited

U.S. PATENT DOCUMENTS

| | | | |
|---|---|---|---|
| 1,985,424 | 12/1934 | Piggott | 260/124 |
| 2,016,962 | 10/1935 | Flint et al. | 260/127 |
| 2,703,798 | 3/1955 | Schwartz | 260/211 |
| 4,623,471 | 11/1986 | Wilsberg | 252/8.8 |
| 4,767,617 | 8/1988 | Shansky et al. | 424/71 |
| 5,374,716 | 12/1994 | Biermann et al. | 536/18.6 |
| 5,547,661 | 8/1996 | Sun et al. | 424/66 |
| 5,576,425 | 11/1996 | Hill et al. | 536/18.6 |

FOREIGN PATENT DOCUMENTS

| | | |
|---|---|---|
| 0 301 298 | 2/1989 | European Pat. Off. . |
| 0 510 870 | 10/1992 | European Pat. Off. . |
| 0 569 843 | 11/1993 | European Pat. Off. . |
| 6-017088 | 10/1994 | Japan . |
| WO90/03977 | 4/1990 | WIPO . |
| WO92/06984 | 4/1992 | WIPO . |
| WO94 24248 | 10/1994 | WIPO . |

OTHER PUBLICATIONS

Tens. Surf. Det. 25:8–13 (1988).
J. Falbe (ed.) "Surfactants in Consumer Products", Springer Verlag, Berlin, 54–124 (1987).
J. Falbe (ed.) "Katalysatoren, Tenside und Mineralöladditive", Thieme Verlag, Stuttgart, 123–217 (1978).

*Primary Examiner*—Thurman K. Page
*Assistant Examiner*—Kathryne E. Shelborne
*Attorney, Agent, or Firm*—Ernest G. Szoke; Wayne C. Jaeschke; Glenn E. J. Murphy

[57] ABSTRACT

The invention relates to opacifiers containing waxes and a mixture of two emulsifiers with different HLB values. The low-viscosity opacifier concentrates are based on waxes with a solids content of 40 to 60% by weight which are characterized that they contain at least one hydrophilic nonionic surfactant with an HLB value above 10 and at least one hydrophobic nonionic surfactant with ab HLB value below 10 as emulsifiers.

35 Claims, No Drawings

LOW-VISCOSITY OPACIFIER CONCENTRATES

FIELD OF THE INVENTION

This invention relates to opacifiers containing waxes and a mixture of two emulsifiers with different HLB values.

PRIOR ART

In the formulation of a number of surface-active domestic products, such as for example dishwashing detergents or hair shampoos, particular emphasis is placed on the fact that the products are clear and do not cloud, even in storage. In other cases, products which are cloudy and show a shimmering effect, so-called "pearlescence", are required for the same purpose. A third group of products is produced with a non-pearlescent white haze, in which case so-called opacifiers are used.

In one particularly advantageous embodiment of the invention, the concentrates contain sugar surfactants as hydrophilic surfactants and fatty acid partial glycerides as hydrophobic surfactants in a ratio by weight of 15:1 to 8:1.

Opacifiers are fine-particle dispersions of polymers or solids which, apart from water and/or a polyol (for example glycerol), essentially contain only a wax and a suitable emulsifier. Opacifiers have to meet various requirements. Particular attention is directed, for example, to the solids content which, on the one hand, should be as high as possible to save storage costs but which, on the other hand, has to be low enough to ensure satisfactory rheological behavior of the product. In addition, it is particularly important that the particles of the dispersion should be very fine so that gradual sedimentation is prevented. In addition, a white haze with no pearlescent effect should be formed.

Accordingly, the complex problem addressed by the present invention was to provide opacifier concentrates based on waxes which would be highly concentrated, but low in viscosity, which would produce a white haze in aqueous surfactant solutions and which would be sufficiently stable in storage by virtue of their particle fineness.

DESCRIPTION OF THE INVENTION

The present invention relates to low-viscosity opacifier concentrates based on waxes with a solids content of 40 to 60% by weight which are characterized in that they contain at least one hydrophilic nonionic surfactant with an HLB value above 10 and at least one hydrophobic nonionic surfactant with an HLB value below 10 as emulsifiers.

It has surprisingly been found that it is only the use of mixtures of hydrophilic and hydrophobic nonionic surfactants as the emulsifier system which leads to particularly fine-particle low-viscosity products which, on introduction into surfactant solutions, produce the required white haze instead of the expected pearlescence.

Waxes

Basically, the choice of the wax is not critical. Typical examples are alkylene glycol fatty acid esters, wax esters, hydrogenated triglycerides, saturated fatty alcohols containing 16 to 18 carbon atoms, ethylene oxide adducts with fatty acids containing 16 to 18 carbon atoms and/or paraffin waxes.

Alkylene glycol fatty acid esters

Another preferred embodiment of the invention is characterized by the use as waxes of alkylene glycol fatty acid esters corresponding to formula (I):

$$R^1CO-O-(A)-O-R^2 \quad (I)$$

in which $R^1CO$ is an aliphatic acyl radical containing 6 to 22 carbon atoms and 0 and/or 1, 2 or 3 double bonds, $R^2$ is $R^1CO$ or is a hydrogen and A is a linear or branched, optionally hydroxy-substituted alkylene group containing 2 to 5 carbon atoms.

These waxes are preferably esters of ethylene glycol or propylene glycol with caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. It is particularly preferred to use ethylene glycol distearate. The quantity of alkylene glycol fatty acid ester used may be from 10 to 30% by weight and is preferably from 15 to 25% by weight, based on the concentrate.

Alkyl and/or alkenyl oligoglycosides

Suitable hydrophilic sugar surfactants with an HLB value above 10 are, for example, alkyl and alkenyl oligoglycosides which are known substances corresponding to formula (II):

$$R^3O-(G)_p \quad (II)$$

where $R^3$ is an alkyl and/or alkenyl radical containing 4 to 22 carbon atoms, G is a sugar unit containing 5 or 6 carbon atoms and p is a number of 1 to 10, and which may be obtained by the relevant methods of preparative organic chemistry. EP-A 0 301 298 and WO 90/03977 are cited as representative of the extensive literature available on the subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides.

The index p in general formula (II) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^3$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ cocofatty alcohol by distillation and which may contain less than 6% by weight of $C_{12}$ alcohol as an impurity, and also alkyl oligoglucosides based on technical $C_{9/11}$ oxoalcohols (DP=1 to 3) are. preferred.

In addition, the alkyl or alkenyl radical $R^3$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and technical mixtures thereof which may be obtained as described above. Alkyl oligoglucosides based on hydrogenated $C_{12/14}$ cocofatty alcohol having a DP of 1 to 3 are preferred.

Fatty acid-N-alkyl polyhydroxyalkylamides

Suitable other hydrophilic sugar surfactants are fatty acid-N-alkyl polyhydroxyalkylamides correspond to formula (III):

in which $R^4CO$ is an aliphatic acyl radical containing 6 to 22 carbon atoms, $R^5$ is hydrogen, an alkyl or hydroxyalkyl radical containing 1 to 4 carbon atoms and [Z] is a linear or branched polyhydroxyalkyl radical containing 3 to 12 carbon atoms and 3 to 10 hydroxyl groups.

The fatty acid-N-alkyl polyhydroxyalkylamides are known compounds which may normally be obtained by reductive amination of a reducing sugar with ammonia, an alkylamine or an alkanolamine and subsequent acylation with a fatty acid, a fatty acid alkyl ester or a fatty acid chloride. Processes for their production are described in U.S. Pat. No. 1,985,424, in U.S. Pat. No. 2,016,962 and in U.S. Pat. No. 2,703,798 and in International patent application WO 92/06984. An overview of this subject by H. Kelkenberg can be found in Tens. Surf. Det. 25, 8 (1988).

The fatty acid-N-alkyl polyhydroxyalkylamides are preferably derived from reducing sugars containing 5 or 6 carbon atoms, more particularly from glucose. Accordingly, the preferred fatty acid-N-alkyl polyhydroxyalkylamides are fatty acid-N-alkyl glucamides which correspond to formula (IV):

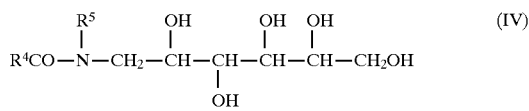

Preferred fatty acid-N-alkyl polyhydroxyalkylamides are glucamides corresponding to formula (IV) in which $R^5$ is hydrogen or an alkyl group and $R^4CO$ represents the acyl component of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid or erucic acid or technical mixtures thereof. Fatty acid-N-alkyl glucamides (IV) obtained by reductive amination of glucose with methylamine and subsequent acylation with lauric acid or $C_{12/14}$ cocofatty acid or a corresponding derivative are particularly preferred. In addition, the polyhydroxyalkylamides may also be derived from maltose and palatinose.

The hydrophilic emulsifiers in general and the sugar surfactants in particular may be used in quantities of 5 to 15% by weight and preferably in quantities of 7.5 to 12.5% by weight, based on the concentrate.

Fatty acid partial glycerides

Fatty acid partial glycerides, which may be used as the hydrophobic emulsifier component with an HLB value below 10, are monoglycerides or diglycerides and technical mixtures of both and correspond to formula (V):

where $R^6CO$ is an aliphatic acyl radical containing 6 to 22 carbon atoms and 0 and/or 1, 2 or 3 double bonds and $R^7$ and $R^8$ independently of one another represent hydrogen or have the same meaning as $R^6CO$, with the proviso that at least one of the two substituents $R^7$ and $R^8$ is hydrogen.

Typical examples are monoesters and diesters of glycerol with caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids. Technical monoglycerides based on lauric acid, oleic acid or stearic acid and on cocofatty acid or tallow fatty acid are particularly preferred from the applicational point of view. The hydrophobic co-emulsifiers in general and the fatty acid partial glycerides in particular may be used in quantities of 1 to 5% by weight and preferably in quantities of 1.5 to 3% by weight, based on the concentrate.

Commercial Applications

The opacifier concentrates according to the invention have a solids content of 40 to 60% by weight and, more particularly, 45 to 55% by weight. They are distinguished by low viscosity, by good flow and pumping properties and by particular particle fineness of the crystals in the dispersion. Accordingly, another advantage of the opacifiers lies in their high stability to sedimentation in the event of prolonged storage. In quantities of 0.5 to 5% by weight and preferably 1 to 2% by weight, based on the water-containing surface-active formulation, such as for example a manual dishwashing detergent, hair shampoo, shower bath or the like, the opacifiers produce a permanent and uniform white haze without any pearlescent effect.

The choice of the surfactants, in whose aqueous solutions the opacifiers according to the invention produce a white haze, is not critical because the onset of the effect is largely independent of the nature of the surfactant component. Accordingly, the opacifiers may be used in aqueous solutions of anionic, nonionic, cationic and/or amphoteric or zwitterionic surfactants.

Typical examples of anionic surfactants are alkylbenzenesulfonates, alkanesulfonates, olefin sulfonates, alkylether sulfonates, glycerol ether sulfonates, α-methyl ester sulfonates, sulfofatty acids, alkylsulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, acyl lactylates, acyl glutamates, acyl tartrates, alkyl oligoglucoside sulfates, protein fatty acid condensates (particularly vegetable products based on soya) and alkyl(ether) phosphates. If the anionic surfactants contain polyglycol ether chains, they may have a conventional homolog distribution although they preferably have a narrow-range homolog distribution.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, alk(en)yl oligoglycosides, fatty acid-N-alkyl glucamides, protein hydrolyzates (particularly vegetable products based on soya), polyol fatty acid esters, sugar esters, sorbitan esters and polysorbates. If the nonionic surfactants contain polyglycol ether chains, they may have a conventional homolog distribution, although they preferably have a narrow-range homolog distribution.

Typical examples of cationic surfactants are quaternary ammonium compounds and esterquats, more particularly quaternized fatty acid trialkanolamine ester salts.

Typical examples of amphoteric or zwitterionic surfactants are alkylbetaines, alkylamidobetaines, aminopropionates, aminoglycinates, imidazolinium betaines and sulfobetaines.

The surfactants mentioned are all known compounds. Information on their structure and production can be found in relevant synoptic works, cf. for example J. Falbe (ed.), "Surfactants In Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123–217.

The concentrates according to the invention may also contain oils such as, for example, Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{16-18}$ fatty alcohols, esters of linear $C_{10-18}$ fatty acids with branched alcohols, more particularly 2-ethylhexanol, esters of linear and/or branched fatty acids with polyhydric alcohols (for example dimer diol or trimer diol) and/or Guerbet alcohols, triglycerides based on $C_{6-10}$ fatty acids, vegetable oils, branched primary alcohols, substituted cyclohexanes, Guerbet carbonates and/or dialkyl ethers.

The opacifiers may be added to the aqueous surfactant solutions either immediately or after mixing with other formulation ingredients, the surfactant solutions having a solids content of 1 to 60% by weight and preferably 5 to 35% by weight, based on the solutions.

EXAMPLES

I. Substances used

A) Ethylene glycol distearate (Cutina® K2 2747)

B) Cocoalkyl glucoside (Plantaren® APG 1200)

C) Lauric acid monoglyceride (Monomuls® 90-L 12)

The wax and the two emulsifiers were made up to 100 parts by weight with 51.6 parts by weight of water, 5 parts by weight of glycerol and 0.5 part by weight of benzoic acid. The viscosity was determined by the Brookfield method (23° C., spindle 5, 10 r.p.m.) and the particle fineness was visually evaluated under a microscope on a scale of 1=very fine crystals to 5=coarse crystals. The results are set out in Table 1 (percentages as % by weight):

TABLE 1

| Ex. | Opacifier c[A] % | c[B] % | c[C] % | B:C | Viscosity Pa*s | Fineness |
|---|---|---|---|---|---|---|
| 1 | 25 | 9.1 | 0.9 | 10:1 | 9 | 1–2 |
| C1 | 25 | 10.0 | — | — | >40 | 5 |
| C2 | 25 | 9.5 | 0.5 | 20:1 | >40 | 3–4 |
| C3 | 25 | 8.8 | 1.2 | 7:1 | 14 | 3 |
| C4 | 25 | 8.3 | 1.7 | 5:1 | 26 | 4 |
| C5 | 25 | 7.5 | 2.5 | 3:1 | >40 | 5 |

We claim:

1. A low-viscosity opacifier concentrate comprising a wax, a hydrophilic nonionic sugar surfactant having an HLB value above 10, and a hydrophobic nonionic fatty acid partial glyceride surfactant having an HLB value below 10, wherein the weight ratio of sugar surfactant to fatty acid partial glyceride is 8:1 to 15:1, and wherein the concentrate has a solids content of 40% to 60% by weight.

2. A concentrate according to claim 1, wherein the wax is selected from the group consisting of alkylene glycol fatty acid esters, wax esters, hydrogenated triglycerides, $C_{16}$ to $C_{18}$ saturated fatty alcohols, ethylene oxide adducts with $C_{16}$–$C_{18}$ fatty acids, and paraffin waxes.

3. A concentrate according to claim 1, wherein the wax is an alkylene glycol fatty acid ester of the formula (I):

$$R^1CO—O—(A)—O—R^2 \qquad (I)$$

wherein $R^1CO$ is a $C_6$ to $C_{22}$ aliphatic acyl group having 0 to 3 double bonds, $R^2$ is $R^1CO$ or hydrogen, and A is a $C_2$ to $C_5$ linear or branched alkylene group that optionally is substituted by a hydroxyl group.

4. A concentrate according to claim 3, wherein the alkylene glycol fatty acid ester is an ester of ethylene glycol or propylene glycol and an acid selected from the group consisting of caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid, and erucic acid.

5. A concentrate according to claim 4, wherein the alkylene glycol fatty acid ester is ethylene glycol distearate.

6. A concentrate according to claim 3, comprising 10% to 30% by weight of the alkylene glycol fatty acid ester.

7. A concentrate according to claim 4, comprising 15% to 25% by weight of the alkylene glycol fatty acid ester.

8. A concentrate according to claim 1, where the sugar surfactant is a compound of the formula (II):

$$R^3O—(G)_p \qquad (II)$$

wherein $R^3$ is $C_4$ to $C_{22}$ alkyl or alkenyl, G is a sugar unit having 5 or 6 carbon atoms, and p is a number of 1 to 10.

9. A concentrate according to claim 8, wherein the sugar unit is and aldose or ketose.

10. A concentrate according to claim 9, wherein the sugar unit is glucose.

11. A concentrate according to claim 8, wherein p is a number of 1 to 6.

12. A concentrate according to claim 11, wherein p is a number of 1.1 to 3.0.

13. A concentrate according to claim 10, wherein p is a number of less than 1.7.

14. A concentrate according to claim 12, wherein p is a number of 1.2 to 1.4.

15. A concentrate according to claim 8, wherein $R^3$ is $C_4$ to $C_{11}$ alkyl or alkenyl.

16. A concentrate according to claim 15, wherein $R^3$ is $C_8$ to $C_{11}$ alkyl or alkenyl.

17. A concentrate according to claim 8, wherein $R^3$ is $C_{12}$ to $C_{14}$ alkyl or alkenyl.

18. A concentrate according to claim 1 wherein the sugar surfactant is a compound of the formula (II):

$$R^3O\text{—}(G)_p \qquad (II)$$

wherein $R^3$ is derived from a primary alcohol selected from the group consisting of butanol, caproic alcohol, caprylic alcohol, capric alcohol, undecyl alcohol, $C_8$ to $C_{18}$ cocofatty alcohol, $C_9$ to $C_{11}$ oxoalcohols, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, and erucyl alcohol, G is a sugar unit having 5 or 6 carbon atoms, and p is a number of 1 to 10.

19. A concentrate according to claim 18, wherein $R^3$ is derived from $C_9$ to $C_{11}$ oxoalcohols or $C_{12}$ to $C_{14}$ cocofatty alcohols, said oxoalcohols or cocofatty alcohols having a DP of 1 to 3.

20. A concentrate according to claim 1, wherein the sugar surfactant is an acid-N-alkylpolyhydroxyalkylamide of the formula (III):

$$\begin{array}{c} R^5 \\ | \\ R^4CO\text{—}N\text{—}(Z) \end{array} \qquad (III)$$

wherein $R^4CO$ is $C_6$ to $C_{22}$ aliphatic acyl, $R^5$ is hydrogen, $C_1$ to $C_4$ alkyl, or $C_1$ to $C_4$ hydroxyalkyl, and (Z) is $C_3$ to $C_{12}$ linear or branched polyhydroxyalkyl having 3 to 10 hydroxyl groups.

21. A concentrate according to claim 20, wherein the acid-N-alkylpolyhydroxyalkylamide is a fatty acid-N-alkyl glucamide of the formula (IV):

$$\begin{array}{c} R^5 \quad\; OH \quad\;\; OH\; OH \\ |\qquad |\qquad\; |\;\;\; | \\ R^4CO\text{—}N\text{—}CH_2\text{—}CH\text{—}CH\text{—}CH\text{—}CH_2OH \\ | \\ OH \end{array} \qquad (IV)$$

wherein $R^5$ is hydrogen or alkyl and $R^4CO$ is the acyl component of an acid selected from the group consisting of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid, or erucic acid.

22. A concentrate according to claim 8, comprising 5% to 15% by weight of the sugar surfactant.

23. A concentrate according to claim 22, comprising 7.5% to 12.5% by weight of the sugar surfactant.

24. A concentrate according to claim 18, comprising 5% to 15% by weight of the sugar surfactant.

25. A concentrate according to claim 24, comprising 7.5% to 12.5% by weight of the sugar surfactant.

26. A concentrate according to claim 20, comprising 5% to 15% by weight of the sugar surfactant.

27. A concentrate according to claim 26 comprising 7.5% to 12.5% by weight of the sugar surfactant.

28. A concentrate according to claim 21, comprising 5% to 15% by weight of the sugar surfactant.

29. A concentrate according to claim 28, comprising 7.5% to 12.5% by weight of the sugar surfactant.

30. A concentrate according to claim 1, wherein the fatty acid partial glyceride is a compound of the formula (V):

$$\begin{array}{c} CH_2O\text{—}COR^6 \\ | \\ CH\text{—}OR^7 \\ | \\ CH_2OR^8 \end{array} \qquad (V)$$

wherein $R^6CO$ is a $C_6$ to $C_{22}$ aliphatic acyl group having 0 to 3 double bonds, and $R^7$ and $R^8$ independently are $R^6CO$ or hydrogen, provided that at least one of $R^7$ and $R^8$ is hydrogen.

31. A concentrate according to claim 1, wherein the fatty acid partial glyceride is a monoester or diester of glycerol with an acid selected from the group consisting of caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid, erucic acid, cocofatty acid, and tallow fatty acid.

32. A concentrate according to claim 30, comprising 1% to 5% by weight of the fatty acid partial glyceride.

33. A concentrate according to claim 32, comprising 1.5% to 3% by weight of the fatty acid partial glyceride.

34. A concentrate according to claim 31, comprising 1% to 5% by weight of the fatty acid triglyceride.

35. A concentrate according to claim 32, comprising 1.5% to 3% weight of the fatty acid triglyceride.

* * * * *